(12) United States Patent
Riddell et al.

(10) Patent No.: US 10,342,505 B2
(45) Date of Patent: Jul. 9, 2019

(54) SYSTEM AND METHOD FOR ADJUSTING A RADIATION DOSE DURING IMAGING OF AN OBJECT WITHIN A SUBJECT

(71) Applicant: General Electric Company, Schenectady, NY (US)

(72) Inventors: Cyril Riddell, Issy-les-Moulineaux (FR); Régis Vaillant, Villebon sur Yvette (FR); Ketan Shrinkant Bacchuwar, Paris (FR)

(73) Assignee: General Electric Company, Schenectady, NY (US)

( * ) Notice: Subject to any disclaimer, the term of this patent is extended or adjusted under 35 U.S.C. 154(b) by 412 days.

(21) Appl. No.: 15/087,304

(22) Filed: Mar. 31, 2016

(65) Prior Publication Data

US 2017/0281114 A1 Oct. 5, 2017

(51) Int. Cl.
*H05G 1/10* (2006.01)
*A61B 6/04* (2006.01)
*A61B 6/00* (2006.01)
*A61B 6/06* (2006.01)
*A61B 6/12* (2006.01)
*G06T 7/00* (2017.01)

(52) U.S. Cl.
CPC .............. *A61B 6/542* (2013.01); *A61B 6/06* (2013.01); *A61B 6/12* (2013.01); *A61B 6/405* (2013.01); *A61B 6/481* (2013.01); *A61B 6/487* (2013.01); *A61B 6/504* (2013.01); *A61B 6/5211* (2013.01); *G06T 7/0012* (2013.01)

(58) Field of Classification Search
CPC combination set(s) only.
See application file for complete search history.

(56) References Cited

U.S. PATENT DOCUMENTS

| 7,471,767 | B2 | 12/2008 | Spahn |
| 2013/0343631 | A1 | 12/2013 | Florent et al. |
| 2014/0161331 | A1 | 6/2014 | Cohen et al. |
| 2015/0139382 | A1 | 5/2015 | Hyung et al. |
| 2015/0366525 | A1* | 12/2015 | Sandholm .............. A61B 6/469 378/4 |

FOREIGN PATENT DOCUMENTS

| EP | 2822469 A2 | 1/2015 |
| WO | 2004/010381 A1 | 1/2004 |
| WO | 2016/200370 A1 | 12/2016 |

OTHER PUBLICATIONS

Extended European Search Report and Opinion issued in connection with corresponding EP Application No. 16205163.5 dated Dec. 4, 2017.

\* cited by examiner

*Primary Examiner* — Don K Wong
(74) *Attorney, Agent, or Firm* — Grogan, Tuccillo & Vanderleeden, LLP

(57) ABSTRACT

A method for adjusting a radiation dose during imaging of an object within a subject is provided. The method includes identifying a task in a first frame that contains the object, the first frame generated via exposing the subject to a radiation beam; and adjusting the radiation beam based at least in part on the task prior to generating a second frame that contains the object, the second frame generated via exposing the subject to the radiation beam.

21 Claims, 5 Drawing Sheets

SYSTEM AND METHOD FOR ADJUSTING A RADIATION DOSE DURING IMAGING OF AN OBJECT WITHIN A SUBJECT

BACKGROUND

Technical Field

Embodiments of the invention relate generally to visualizing objects within an imaged subject.

Discussion of Art

Imaging systems used by physicians to perform diagnostic analysis and therapeutic procedures produce images by exposing a patient to radiation such as x-rays. Typically, the larger the amount of radiation used during an imaging procedure, the better the image quality of the produced images. Exposure to certain types of radiation, however, can potentially cause unwanted sides effects in the patient. As a result, many imaging systems seek to conserve the total amount of radiation used during an imaging procedure, i.e., the "radiation dose" of the imaging procedure. The radiation dose afforded by an imaging system for a particular imaging procedure is known as the imaging system's efficiency. For example, an imaging system that is more efficient than other imaging systems will have a lower radiation dose while achieving the same and/or better image quality than the other imaging systems for the same imaging procedure.

Many imaging systems seek to reduce the radiation dose of an imaging procedure by allowing a physician to manually adjust the amount of radiation used to generate a series of images during an imaging procedure. For example, many imaging systems typically allow a physician to increase and/or decrease the amount of radiation used to produce images as required, e.g., using a high amount of radiation during parts of an imaging procedure that require high resolution; and using a low amount of radiation when low resolution images, or no images, will suffice. Once an imaging procedure is underway, however, it is often the case that a physician is too preoccupied with other aspects of the imaging procedure to efficiently adjust the amount of radiation as needed.

Accordingly, many imaging systems use automated control loops that adjust the amount of radiation based on noise and average brightness levels measured in the produced images. Systems that measure noise and average brightness levels, however, often fail to identify parts/steps of an imaging procedure where image quality may be reduced and/or increased as the difficulty level, i.e., the need for high quality imagery, of the imaging procedure changes. As a result, many imaging systems often miss opportunities to reduce the radiation dose of an imaging procedure. Moreover, in many imaging systems, the only operating parameter modulated to reduce the radiation dose of a particular imaging procedure is the amount/intensity of radiation used to generate one or more images.

What is needed, therefore, is a system and method for adjusting a radiation dose during imaging of an object within a subject to improve efficiency.

BRIEF DESCRIPTION

In an embodiment, a method for adjusting a radiation dose during imaging of an object within a subject is provided. The method includes identifying a task in a first frame that contains the object, the first frame generated via exposing the subject to a radiation beam; and adjusting the radiation beam based at least in part on the task prior to generating a second frame that contains the object, the second frame generated via exposing the subject to the radiation beam.

In yet another embodiment, another method for adjusting a radiation dose during imaging of an object within a subject is provided. The method includes generating a first frame that contains the object via applying a mask to a first image obtained via exposing the subject to a radiation beam. The method further includes identifying a task in the first frame. The method further includes generating a second frame that contains the object via applying the mask to a second image obtained via exposing the subject to the radiation beam. The method further includes comparing the first frame with the second frame to obtain a contrast indicator. The method further includes adjusting the mask based at least in part on the contrast indicator. The method further includes adjusting the radiation beam based at least in part on at least one of the task and the adjusted mask.

In yet another embodiment, an imaging system that adjusts a radiation dose during imaging of an object within a subject is provided. The system includes a controller configured to generate a first frame that contains the object via exposing the subject to a radiation beam. The controller is further configured to identify a task in the first frame and adjust the radiation beam based at least in part on the identified task prior to generating a second frame that contains the object via exposing the subject to the radiation beam.

In yet another embodiment, another method for adjusting a radiation dose during imaging of an object within a subject is provided. The method includes acquiring a first series of images in rotation around the subject prior to injection of a contrast agent; and acquiring a second series of images in rotation around the subject after injection of the contract agent. A pattern is identified in a first image of the second series of images, and subsequent images of the second series of images acquired after the first image are optimized based at least in part on the identified pattern.

DRAWINGS

The present invention will be better understood from reading the following description of non-limiting embodiments, with reference to the attached drawings, wherein below:

DETAILED DESCRIPTION

Figure 1:
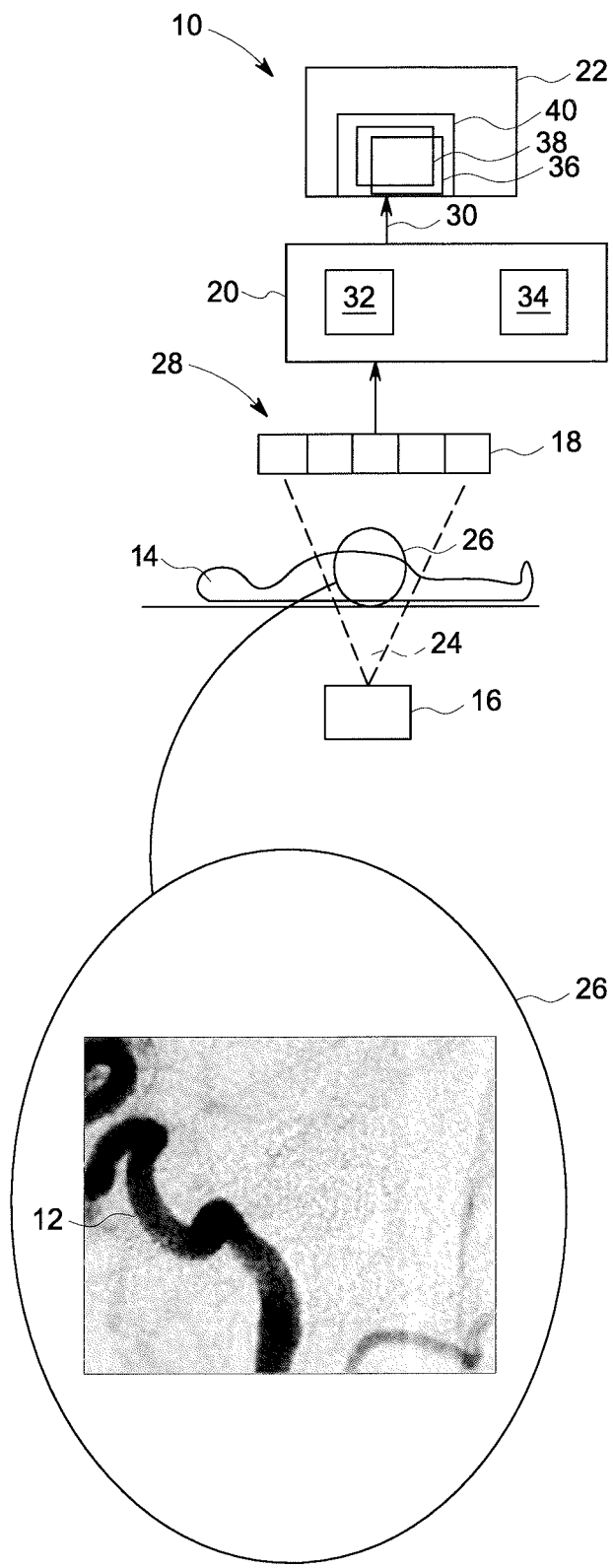
FIG. 1 is a block diagram of an exemplary imaging system for adjusting a radiation dose during imaging of an object within a subject in accordance with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. As also used herein, the term "real time" means a level of processing responsiveness that a user senses as sufficiently immediate or that enables the processor to keep up with an external process. As further used herein, the term "imaging procedure" refers to a medical procedure that involves an imaging system to assist in accomplishing one or more tasks. Accordingly, as also used herein, the term "task" means an objective of a medical procedure, e.g., deploying/installing a stent into a blood vessel, locating an ulcer, imaging a clogged artery, suturing a patient, and/or other medical processes. Such tasks may include imaging large highly contrasted blood vessels and/or small low contrast blood vessels.

Additionally, while the embodiments disclosed herein are described with respect to a fluoroscopic imaging systems, it is to be understood that embodiments of the present invention are equally applicable to devices such as Magnetic Resonance Imaging ("MRI"), real time endoscopic imaging, an/or any other type of imaging where multiple images are acquired in order to produce a visual representation of one or more objects within an imaged subject. As will be appreciated, embodiments of the present invention related imaging systems may be used to analyze objects within any material which can be internally imaged, generally. As such, embodiments of the present invention are not limited to analyzing objects within human tissue.

Referring to FIG. 1, an imaging system 10 for adjusting a radiation dose during imaging of at least one object 12 within a subject 14 is shown. The system 10 includes a radiation source 16, a detector 18, a controller 20, and a display screen 22. The radiation source 16 projects a radiation beam 24 through an area of interest 26 of the imaged subject 14 within which the object 12 is disposed. The radiation beam 24 is received by the detector 18, which generates a plurality of images 28 that are then communicated to the controller 20, which generates a video feed 30 that is transmitted to and displayed by the display screen 22. As is to be appreciated, in embodiments, the imaging system 10 may perform fluoroscopic, 3D Spin, and/or a Digital Subtraction Angiography "DSA" procedures, and/or any other type of imaging procedure that utilizes radiation. Further, the imaged object 12 may be one or more blood vessels or other bodily organs that have been infused/injected with a high contrasting-medium, e.g. iodine; and/or a medical device. For example, as shown in FIG. 1, the imaged subject 14 may be a patient undergoing an angioplasty procedure, and the imaged object 12 may be a blood vessel into which a stent is to be deployed.

As further shown in FIG. 1, the controller 20 includes at least one processor/CPU 32 and at least one memory device 34, and is in electronic communication with both the detector 18 and the display screen 22. In embodiments, the controller 20 may be in further electronic communication with the radiation source 16. An imaging program/application may be stored in the at least one memory device 34 that, when loaded into the at least one processor 32, adapts the controller 20 to generate the video feed 30 by processing the images 28 received from the detector 18. In embodiments, the imaging program may further adapt the controller 20 to control the detector 18 and/or the radiation source 16.

The video feed 30 includes a plurality of frames 36, 38, and 40. As used herein, the term frame describes a composite image that may be based at least in part on one or more of the plurality of images 28 acquired by the imaging system 10. For instance, in embodiments, a single composite image/frame 36 may be generated by registering one or more of the acquired images 28 to a reference image selected from the plurality of images 28. The registration of one or more images 28 to a reference image increases the contrast of the object 12 within the produced/generated frame 36. Accordingly, in embodiments, each frame 36, 38, and 40 may be based at least in part on one or more of the images 28 received by the controller 20 from the detector 18. Once a frame 36 has been generated, it is transmitted, as part of the video feed 30, by the controller 20 to the display screen 22. In other words, in embodiments, the displayed video feed 30 is a processed form of the raw images 28 acquired by the system 10. In embodiments, the video feed 30 may be a live/real time and/or near-real time feed. In other embodiments, one or more of the frames 36, 38, and 40 may be still images, e.g., a photograph.

Figure 2:
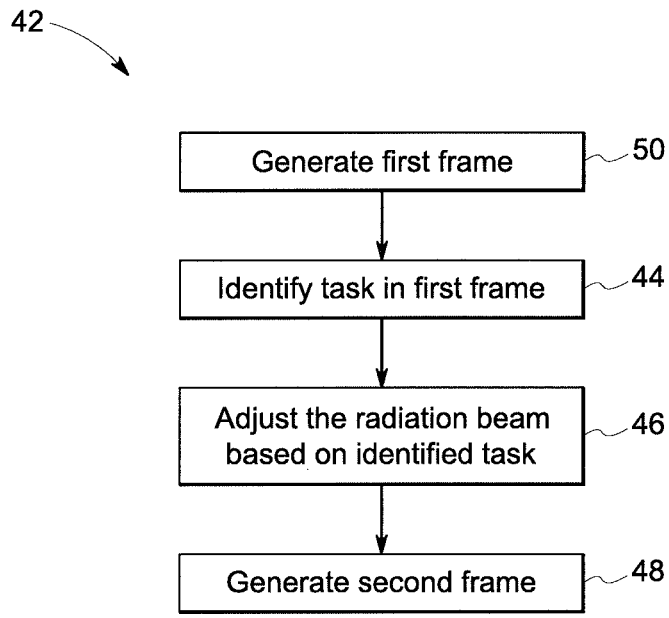
FIG. 2 is a flow chart depicting a method for adjusting a radiation dose during imaging of an object within a subject in accordance with an embodiment of the invention.

Turning now to FIG. 2, a method 42 for adjusting a radiation dose during imaging of the object 12 within the subject 14 that utilizes the system 10 is shown. As is to be appreciated, in embodiments, the imaging application stored in the memory device 34 may be loaded into the at least one processor/CPU 32 such that the controller 20 is further adapted/configured by the imaging application to perform all, or part, of method 42. The method 42 includes identifying 44 a task in a first frame 36 that contains the object 12, and adjusting 46 the radiation beam 24 based at least in part on the task prior to generating 48 a second frame 40 that contains the object 12. As is to be further appreciated, the method 42 may further include generating 50 the first frame 36. By identifying 44 the task being performed in the first frame 36, the system 10 can make a determination as to whether the radiation dose of the procedure can be lowered by adjusting 46 the radiation beam 24. For example, some tasks may be adequately performed with low image quality and/or without the video feed 30 at all. Additionally, while the embodiments depicted in the accompanying figures show identifying 44 the task in a single frame 36, it is to be understood that more than one frame may be used to identify 44 the task.

Figure 3:
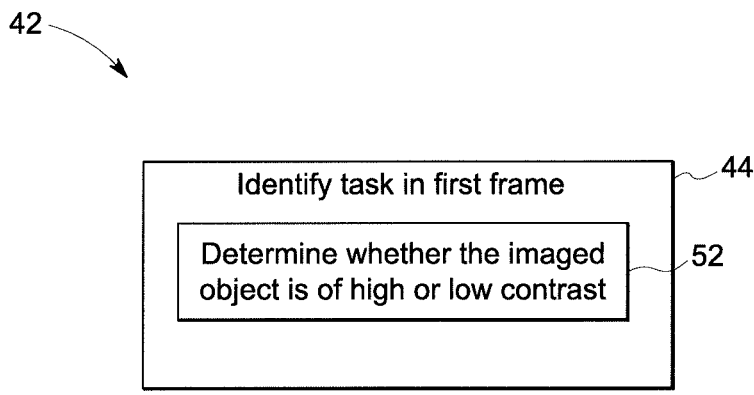
FIG. 3 is another flow chart depicting the method of FIG. 2.

As shown in FIG. 3, identifying 44 the task in the first frame 36 may include determining 52 whether the imaged object 12 is of a high contrast or a low contrast. As used herein the terms "high contrast" and "low contrast" refer to noticeable differences in the object 12 with respect to other structures and/or background noise in one or more of the frames 36, 38, and 40. Examples of high and low contrasting objects include large peripheral vessels (12 in FIG. 7) and small vessels (12 in FIG. 8) that are projected over a bony structure, respectively. High and low contrasting objects may indicate that the task being performed is of low and high difficulty, respectively. In embodiments, the system 10 may also utilize the size, shape, and/or location of the object 12 to determine the task.

Figure 4:
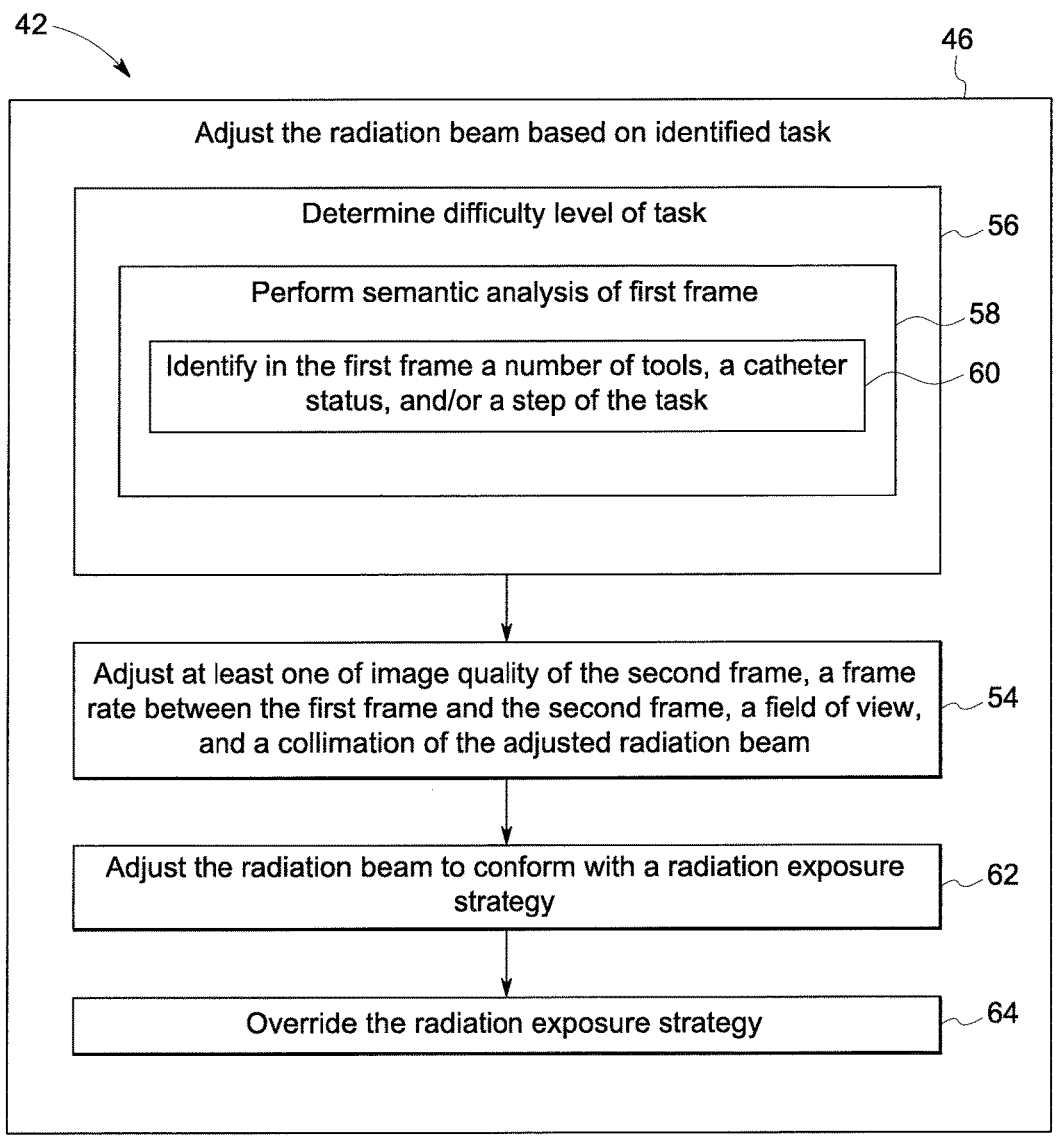
FIG. 4 is yet another flow chart depicting the method of FIG. 2.

As illustrated in FIG. 4, adjusting 46 the radiation beam 24 may include adjusting 54 the image quality of the second frame 40, a frame rate between the first 36 and the second 40 frames, a field of view of the second frame 40, and a collimation of the adjusted radiation beam 24. As used herein, the term "frame rate" refers to the time period between generating 48 and 50 the first 36 and the second 40 frames and/or the time period between obtaining the underlying images 28 from which the frames 36, 38, and 40 are based on. As is to be appreciated, in embodiments, the imaging system 10 may recognize that the image quality and/or frame rate of the generated frames 36, 38, and 40 can be adjusted without affecting the physician's ability to perform the identified task and/or imaging procedure. Lowering the image quality of the frames 36, 38, and 40 in turn allows the image quality of the underlying raw images 28 to be reduced, which further allows the intensity of the radiation beam 24 to be reduced. Lowering the frame rate reduces the total amount of raw images 28 taken by the imaging system 10 during a task, which in turn reduces the total amount of time that the subject/patient 14 is exposed to the radiation beam 24 during an imaging procedure, i.e., lowering the frame rate reduces the radiation dose of the imaging procedure.

For example, an imaging procedure may require a physician to deploy multiple stents into a patient 14. Accordingly, the imaging system 10 may maintain a high image quality and/or frame rate while the physician is deploying a first stent into a first blood vessel, e.g. a task that requires a good visualization/imaging of the object 12. The imaging system 10 may then identify/detect 44 that the physician has finished deploying the first stent and is proceeding to manipulate a different interventional tool in a simple manner, i.e., a task that typically does not require good visualization/imaging of the object 12. Accordingly, the imaging system 10 may adjust/reduce 54 the frame rate and/or the image quality. The imaging system 10 may then identify 44 when the physician begins the next task of deploying the second stent, i.e., a task that requires good visualization/imaging of the object 12, and increase the frame rate and/or the image quality as needed.

As further shown in FIG. 4, in embodiments, adjusting 46 the radiation beam 24 based at least in part on the task prior to generating 48 the second frame 40, may include determining 56 a difficulty level of the task. For example, if the imaging system 10 determines 56 that the identified task is of a high difficulty, such as expanding a stent in a coronary artery, then the imaging system 10 may set/adjust 54 the image quality and/or the frame rate so as to provide a good high quality video feed 30 to the physician. Alternatively, if the imaging system 10 determines 56 that the identified task is not difficult, such as imaging a large high contrasting slow moving medical device located within a non-critical region of the patient's 14 body, the imaging system 10 may adjust/reduce 54 the image quality and/or the frame rate. The imaging system 10 may determine 56 the difficulty level of the task by performing 58 a semantic analysis of the first frame 36.

As used herein, the term "semantic analysis" means analyzing the contents of a frame, as opposed to only analyzing mere statistics such as noise and/or brightness levels. As such, the imaging system 10 may perform 58 the semantic analysis of the first frame 36 by identifying 60 in the first frame 36 at least one of a number of tools, a status of a catheter, and a step of the task being performed. The identified tools may include stents, guide wires, balloons, and/or other types of medical devices which may be inserted into a patient 14 during the imaging procedure. The catheter status may include empty, filled, static, being located at the ostia of a blood vessel, and/or being actively displaced. For example, the imaging system 10 may detect that multiple stents and/or guide wires are being positioned at the junction of two coronary arteries, i.e., a very difficult and complicated task. Based upon the type of items identified 60 in the frame, the imaging system 10 may be able to determine 56 the difficulty of the task being performed by the physician.

As further shown in FIG. 4, adjusting 46 the radiation beam 24 based at least in part on the task prior to generating 48 the second frame 40 may include adjusting 62 the radiation beam 24 such that the adjusted radiation beam 24 conforms to a radiation exposure strategy. For example, in embodiments, the imaging system 10 may allow the physician to input an aggressiveness setting which governs how aggressively the imaging system 10 can attempt to conserve the radiation dose. In order to prevent the imaging system 10 from being too conservative, such that the physician's ability to perform the imaging procedure is impaired, or to correct for situations where the imaging system 10 is applying too much radiation, the imaging system 10 may allow the physician to override 64 the radiation exposure strategy such that the adjusted radiation beam 24 does not conform to the radiation exposure strategy.

Figure 5:
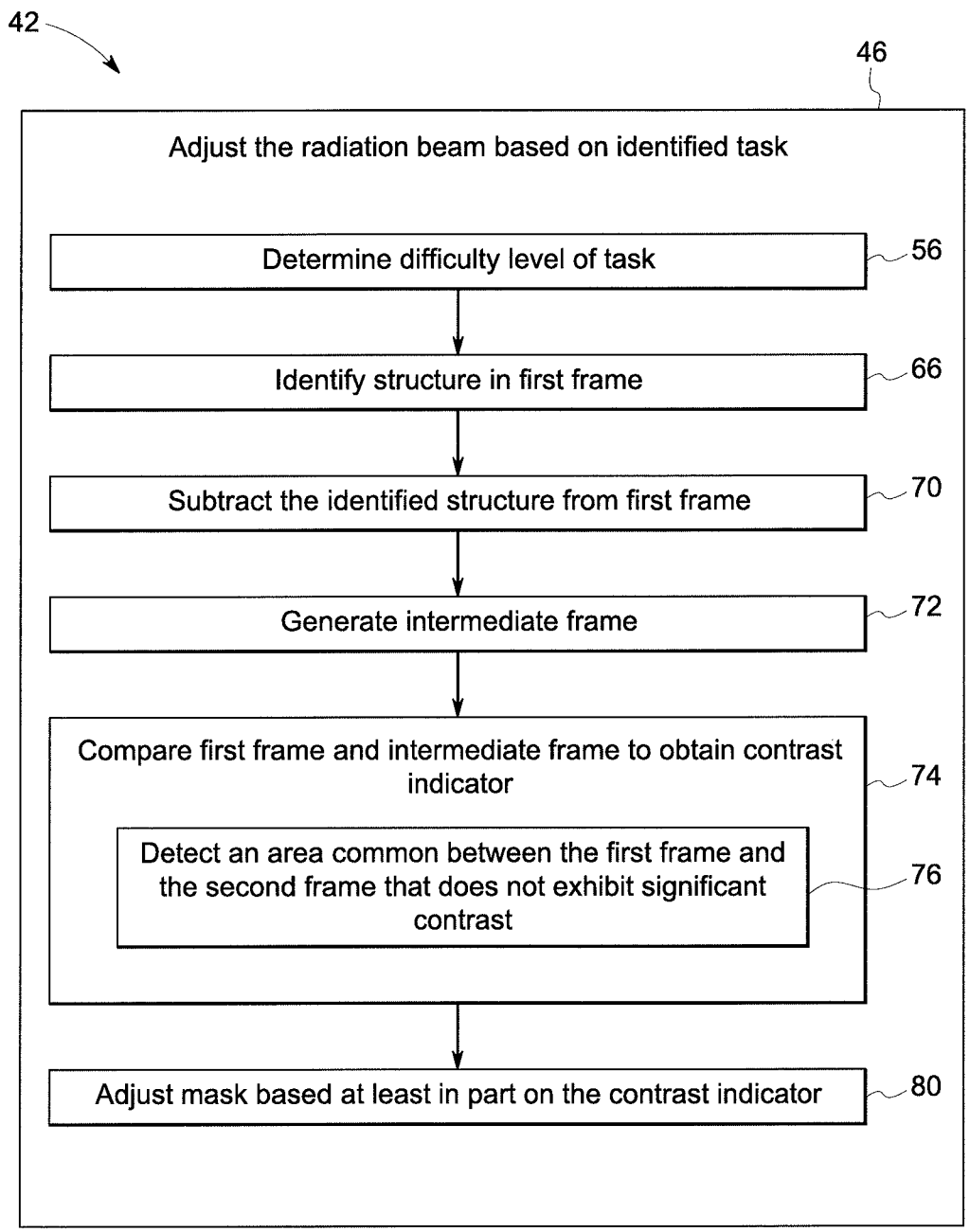
FIG. 5 is still yet another flow chart depicting the method of FIG. 2.
Figure 6:
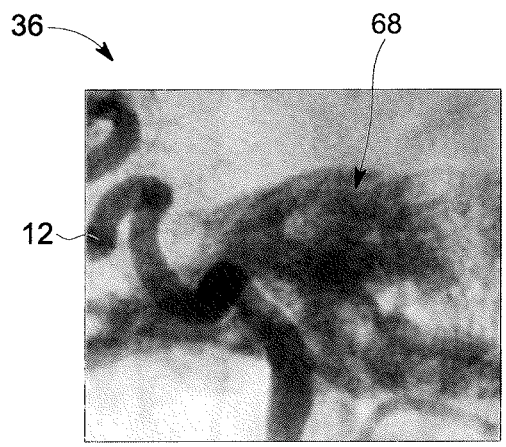
FIG. 6 is a frame of the imaging system of FIG. 1 that depicts the object and a structure in accordance with an embodiment of the invention.
Figure 7:
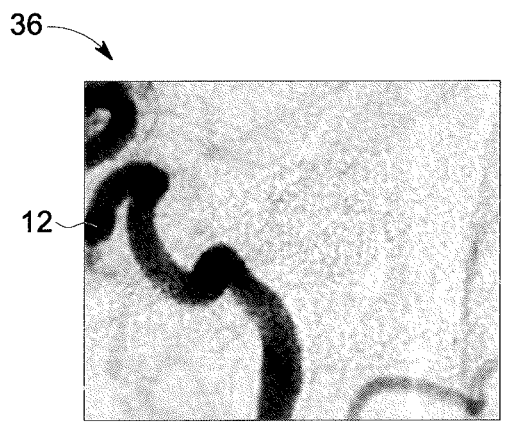
FIG. 7 is the frame of FIG. 6 wherein the structure has been removed via subtraction in accordance with an embodiment of the invention.
Figure 8:
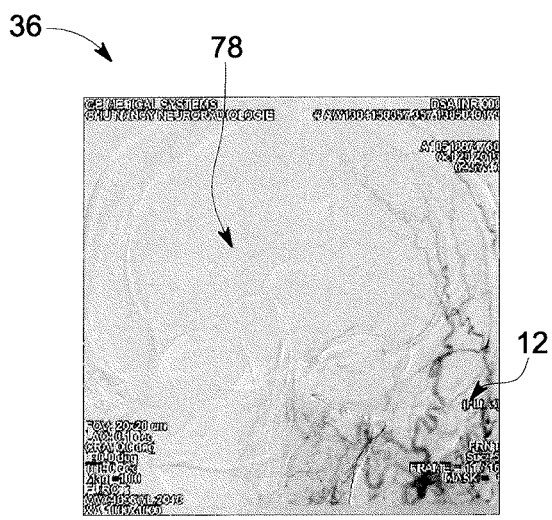
FIG. 8 is another frame of the imaging system of FIG. 1 that depicts the object.

Referring now to FIG. 5, in embodiments, adjusting 46 the radiation beam 24 based at least in part on the task prior to generating 48 the second frame 40 may include identifying 66 a structure (68 in FIG. 6) in the first frame 36, and subtracting 70 the identified structure 68 from the first frame 36 (shown as the absence of the structure 68 in FIG. 7). For example, the imaged object 12 may be one or more brain blood vessels which are surrounded by large areas of dense bone, e.g., structures. By subtracting 70 out the bone from the first frame 36, the intensity of the radiation beam 24 can be adjusted/reduced 46 without reducing the image quality of the second frame 40. In embodiments, subtracting 70 out structures 68 may improve the image quality of the second frame 40 while still allowing for the intensity of the radiation beam 24 to be reduced. As is to be appreciated, subtraction 70 may be based on comparing one or more priori images, i.e., raw images 28 taken prior to injection of a high contrasting medium/dye into the object 12, to raw images 28 taken after injection of the high contrasting dye into the object 12 which may be mathematically equivalent, or substantially mathematically equivalent, to the priori images 28.

Additionally, in embodiments, the frames 36 and 40 may be generated 50 and 48 by applying a background mask, also referred to herein simply as a "mask", to one or more raw images 28. The mask may be based in part on one or more priori images 28 captured prior to injecting a high contrast medium into the objects 12. In embodiments which capture two or more priori images 28, the mask may be produced/generated by averaging the one or more priori images 28, i.e., mask averaging. Applying the produced/generated mask to the raw images 28 captured after the high contrast medium has been injected into the objects 12 may improve the contrast of the objects 12 in the generated frames 36 and 40 by filtering out background imagery, e.g., parts/areas of the raw images 28 used to generate frames 36 and 40 that do not form part of the objects 12 of interest. In such embodiments, improving the contrast of the objects 12 via the mask may allow the radiation dose of the imaging procedure to be reduced by as much as thirty-three percent ("33%").

As is to be further appreciated, while subtracting 70 may remove structure, subtracting 70 may not remove noise, and in some cases, may even add noise. To compensate for the potential of noise resulting from subtraction 70, some embodiments of the present invention may increase the radiation dose required for a frame. Additionally, some embodiments may average, i.e., mask averaging, several frames to decrease the noise in the mask. The number of images averaged may be a parameter that is fixed a priori, since these images are typically acquired prior to injection of a contrast agent. Further, some embodiments of the present invention may analyze parts of images acquired after injection of a contrast agent to determine if they are equivalent to the mask for the purpose of mask averaging, which in turn may provide for adjusting the balance of noise between the mask and the contrast agent, which further provides for the dose of contrast images to be further reduced. For example, in an embodiment, a mask may have a noise variance "n_mask", a contrast image may have a noise variance "n_contrast", and a subtracted image may have a noise variance "n_mask+n_contrast." In such an embodiment, if n_mask=n_contrast=n, noise variance in the subtraction may be 2n. Thus, in some embodiments of the present invention, if and only if one identifies that a first image, acquired after injection of a contrast agent, in fact has no contrast, the mask may be averaged a posteriori giving n_mask=n/2. Thus, keeping a subtraction noise of 2n, a contrast frame can have a noise 2n−n/2=3n/2 instead of 2n−n=n. Thus, a contrast image can have 50% more noise than initially intended, which may correspond to a 33% less dose than initially intended.

Accordingly, and as also shown in FIG. 5, in embodiments that utilize a mask, adjusting 46 the radiation beam 24 based at least in part on the task prior to generating 48 the second frame 40 may include generating 72 an intermediate frame 38 that contains the object 12, and comparing 74 the first frame 36 with the intermediate frame 38 to obtain a contrast indicator. It is to be understood that generating 72 the intermediate frame 38 involves applying the mask to the underlying raw image(s) 28 on which the intermediate image 38 is based on. For example, in embodiments, comparing 74 the first frame 36 to the intermediate frame 38 may include detecting 76 one or more areas (78 in FIG. 8), which do not show significant contrast over several generated frames 36, 38. Such areas may indicate that the mask may be adjusted/reduced 80, e.g., the mask may be adjusted so that it allows more or less background imagery/noise of the underlying images 28 to pass to the generated frame 40, which in turn allows for the intensity of the radiation beam 24 to be adjusted/reduced 46. In other words, large areas common between the first frame 36 and the intermediate frame 38 which show no change in contrast indicate that the mask may be reduced, e.g., reducing the noise in the mask, without significantly degrading the quality of subsequently generated frames. In such embodiments, the radiation beam 24 may be reduced at the exposure of the subsequently generated frames.

It is to be understood, however, that in such embodiments, the initial raw images 28, i.e., the priori images, used to generate the mask may require a large radiation beam 24 intensity setting. As is to be appreciated, however, as the imaging procedure progresses, the imaging system 10 may reduce the intensity of the radiation beam 24 as discussed above. Thus, while embodiments of the imaging system 10 may use higher priori radiation intensity/setting than traditional systems, the imaging system 10 may ultimately use less radiation than traditional systems by reducing the noise in the mask propagating over subsequent frames.

Additionally, in an embodiment which may be implemented with respect to 3D subtraction, two series of images may be acquired in rotation around the patient. In such embodiments, the first rotation may occur prior to the injection of a contrast agent, with the second rotation occurring after injection of the contrast agent. This may be referred to as a "static" acquisition mode, i.e., the acquired images contain the same injection pattern. While changes in the concentration of the contrast agent occur during the rotation due to imperfections, a common pattern may still be discernable and/or assumed among the images. This pattern may cover different areas covered by a detector depending on the angle of the rotation. Typically, a brain hemisphere will have contrast on one side of the detector at the beginning of the rotation, will have contrast that covers the whole detector at mid-rotation, and will cover the opposite side of the detector at the end of the rotation. By knowing the covered area(s) at the beginning, it is possible to know/predict the coverage of other areas at each position of the rotation. Therefore, given the first rotation (prior to injection of the contrast agent) and the first image of the second rotation (in which identification of the contrast pattern can be made), exposure of all the images in the second rotation can be optimized.

It is to be further understood that the imaging system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, the imaging system 10 may include at least one processor 32, system memory 34 including random access memory ("RAM") and read-only memory ("ROM"), an input/output controller, and one or more data storage structures. All of these latter elements may be in communication with the at least one processor 32 to facilitate the operation of the imaging system 10 as discussed above. Suitable computer program code may be provided for executing numerous functions, including those discussed above in connection with the imaging system 10 and methods disclosed herein. The computer program code may also include program elements such as an operating system, a database management system and "device drivers" that allow the imaging system 10, to interface with computer peripheral devices, e.g., sensors, a video display, a keyboard, a computer mouse, etc.

The at least one processor 32 of the imaging system 10 may include one or more conventional microprocessors and one or more supplementary co-processors such as math co-processors or the like. Elements in communication with each other need not be continually signaling or transmitting to each other. On the contrary, such elements may transmit to each other as necessary, may refrain from exchanging data at certain times, and may cause several steps to be performed to establish a communication link there between.

The data storage structures such as memory discussed herein may include an appropriate combination of magnetic, optical and/or semiconductor memory, and may include, for example, RAM, ROM, flash drive, an optical disc such as a compact disc and/or a hard disk or drive. The data storage structures may store, for example, information required by the imaging system 10 and/or one or more programs, e.g., computer program code and/or a computer program product, adapted to direct the imaging system 10. The programs may be stored, for example, in a compressed, an uncompiled and/or an encrypted format, and may include computer program code. The instructions of the computer program code may be read into a main memory of a processor from a computer-readable medium. While execution of sequences of instructions in the program causes the processor to perform the process steps described herein, hard-wired circuitry may be used in place of, or in combination with, software instructions for implementation of the processes of the present invention. Thus, embodiments of the present invention are not limited to any specific combination of hardware and software.

The program may also be implemented in programmable hardware devices such as field programmable gate arrays, programmable array logic, programmable logic devices or the like. Programs may also be implemented in software for execution by various types of computer processors. A program of executable code may, for instance, includes one or more physical or logical blocks of computer instructions, which may, for instance, be organized as an object, procedure, process or function. Nevertheless, the executables of an identified program need not be physically located together, but may include separate instructions stored in different locations which, when joined logically together, form the program and achieve the stated purpose for the programs such as preserving privacy by executing the plurality of random operations. In an embodiment, an application of executable code may be a compilation of many instructions, and may even be distributed over several different code partitions or segments, among different programs, and across several devices.

The term "computer-readable medium" as used herein refers to any medium that provides or participates in providing instructions to at least one processor 32 of the imaging system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

Various forms of computer readable media may be involved in carrying one or more sequences of one or more instructions to at least one processor for execution. For example, the instructions may initially be borne on a magnetic disk of a remote computer (not shown). The remote computer can load the instructions into its dynamic memory and send the instructions over an Ethernet connection, cable line, or telephone line using a modem. A communications device local to a computing device, e.g., a server, can receive the data on the respective communications line and place the data on a system bus for at least one processor. The system bus carries the data to main memory, from which the at least one processor retrieves and executes the instructions. The instructions received by main memory may optionally be stored in memory either before or after execution by the at least one processor. In addition, instructions may be received via a communication port as electrical, electromagnetic or optical signals, which are exemplary forms of wireless communications or data streams that carry various types of information As such, it is to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a method for adjusting a radiation dose during imaging of an object within a subject is provided. The method includes identifying a task in a first frame that contains the object, the first frame generated via exposing the subject to a radiation beam; and adjusting the radiation beam based at least in part on the task prior to generating a second frame that contains the object, the second frame generated via exposing the subject to the radiation beam. In certain embodiments, adjusting the radiation beam based at least in part on the task prior to generating a second frame that contains the object, the second frame generated via exposing the subject to the radiation beam, includes adjusting at least one of an image quality of the second frame, a frame rate between the first frame and the second frame, a field of view of the second frame, and a collimation of the adjusted radiation beam. In certain embodiments, adjusting the radiation beam based at least in part on the task prior to generating a second frame that contains the object, the second frame generated via exposing the subject to the radiation beam, includes determining a difficulty level of the task. In certain embodiments, determining a difficulty level of the task includes performing a semantic analysis of the first frame. In certain embodiments, performing a semantic analysis of the first frame includes identifying in the first frame at least one of a number of tools, a status of a catheter, and a step of the task. In certain embodiments, adjusting the radiation beam based at least in part on the task prior to generating a second frame that contains the object, the second frame generated via exposing the subject to the radiation beam, includes adjusting the radiation beam such that the adjusted radiation beam conforms to a radiation exposure strategy. In certain embodiments, adjusting the radiation beam based at least in part on the task prior to generating a second frame that contains the object, the second frame generated via exposing the subject to the radiation beam, further includes overriding the radiation exposure strategy such that the adjusted radiation beam does not conform to the radiation exposure strategy. In certain embodiments, identifying a task in a first frame that contains the object, the first frame generated via exposing the subject to the radiation beam, includes determining in the first frame whether the imaged object is at least one of high contrast and low contrast. In certain embodiments, adjusting the radiation beam based at least in part on the task prior to generating a second frame that contains the object, the second frame generated via exposing the subject to the radiation beam, includes identifying a structure in the first frame; and subtracting the identified structure from the first frame. In certain embodiments, the subject is a patient, the imaged object is a blood vessel of the patient that is infused with a high contrast medium, and the identified structure includes at least one of an organ of the patient other than the blood vessel, and/or a medical device. In certain embodiments, the first frame and the second frame are based at least in part on a mask, and adjusting the radiation beam based at least in part on the task prior to generating a second frame that contains the object, the second frame generated via exposing the subject to the radiation beam, includes generating an intermediate frame via exposing the subject to the radiation beam before generating the second frame, the intermediate frame containing the object and based at least in part on the mask; comparing the first frame with the intermediate frame to obtain a contrast indicator; and adjusting the mask based at least in part on the contrast indicator.

Other embodiments provide for another method for adjusting a radiation dose during imaging of an object within a subject. The method includes generating a first frame that contains the object via applying a mask to a first image obtained via exposing the subject to a radiation beam. The method further includes identifying a task in the first frame. The method further includes generating a second frame that contains the object via applying the mask to a second image obtained via exposing the subject to the radiation beam. The method further includes comparing the first frame with the second frame to obtain a contrast indicator. The method further includes adjusting the mask based at least in part on the contrast indicator. The method further includes adjusting the radiation beam based at least in part on at least one of the task and the adjusted mask. In certain embodiments, comparing the first frame with the second frame to obtain a contrast indicator includes detecting an area common between the first frame and the second frame that does not exhibit significant contrast. In certain embodiments, adjusting the mask based at least in part on the contrast indicator includes reducing the mask. In certain embodiments, adjusting the radiation beam based at least in part on at least one of the task and the adjusted mask includes identifying a structure in the first frame; and subtracting the identified structure from the first frame.

Yet still other embodiments provide for an imaging system that adjusts a radiation dose during imaging of an object within a subject. The system includes a controller configured to generate a first frame that contains the object via exposing the subject to a radiation beam. The controller is further configured to identify a task in the first frame and adjust the radiation beam based at least in part on the identified task prior to generating a second frame that contains the object via exposing the subject to the radiation beam. In certain embodiments, the subject is a patient, the imaged object is a blood vessel of the patient that is infused with a high contrast medium, and the controller is further configured to determine a difficulty level of the identified task. In certain embodiments, the controller is further configured to determine the difficulty level of the identified task via performing a semantic analysis of the first frame. In certain embodiments, the controller is further configured to adjust the radiation beam via identifying a structure in the first frame and subtracting the identified structure from the first frame. In certain embodiments, the first frame and the second frame are based at least in part on a mask, and the controller is further configured to generate an intermediate frame after generating the first frame and before generating the second frame, the intermediate frame containing the object via exposing the subject to the radiation beam and also based at least in part on the mask; compare the first frame with the intermediate frame to obtain a contrast indicator; adjust the mask based at least in part on the contrast indicator; and adjust the radiation beam based at least in part on the adjusted mask prior to generating the second frame.

Yet still other embodiments provide for another method for adjusting a radiation dose during imaging of an object within a subject. The method includes acquiring a first series of images in rotation around the subject prior to injection of a contrast agent; and acquiring a second series of images in rotation around the subject after injection of the contract agent. A pattern is identified in a first image of the second series of images, and subsequent images of the second series of images acquired after the first image are optimized based at least in part on the identified pattern.

Accordingly, as is to be appreciated, by automatically identifying the task being performed in a frame generated by the imaging system and adjusting the radiation beam, some embodiments of the invention do not require user interaction after initially being configured for the imaging procedure. Thus, some embodiments provide for the ability to recognize and capitalize on opportunities to reduce the radiation dose of an imaging procedure that would otherwise be missed by a physician preoccupied with performing other aspects of the imaging procedure. For example, some embodiments may recognize that the image quality and/or frame rate may be reduced during the initial phase of a fluoroscopic procedure before the high-contrast medium has been injected into the imaged blood vessel. Additionally, some embodiments may recognize that the image quality and/or frame rate may be reduced while the physician is manipulating a medical device that is out of view of the video feed.

Further, by adjusting the frame rate of the video feed, some embodiments of the invention provide for an additional parameter to reduce the radiation dose of an imaging procedure. Further still, by determining the task, and/or the difficulty of the task, via performing a semantic analysis of a frame, some embodiments of the invention provide for the ability to recognize opportunities to adjust the radiation beam that are often missed by traditional imaging systems. Additionally, some embodiments provide for the ability to recognize opportunities to adjust the radiation beam that are often missed by traditional imaging systems without requiring equipment in addition to what is typically found in most modern imaging systems. Moreover, by subtracting structures in accordance with the method described herein, some embodiments which incorporate mask averaging provide for frames to be optimized based on the subtracted features, as opposed to the features of the mask. Accordingly, such embodiments may supplement the adjustment of the collimation of the radiation beam when imaging the area of interest.

As is to be understood, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted based on 35 U.S.C. § 112(f), unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A method for adjusting a radiation dose during imaging of an object within a subject, the method comprising:
   identifying a medical surgical task in a first image frame that contains the object, the first image frame generated via exposing the subject to a radiation beam; and
   adjusting the radiation beam based at least in part on the medical surgical task prior to generating a second image frame that contains the object, the second image frame generated via exposing the subject to the radiation beam.

2. The method of claim 1, wherein adjusting the radiation beam based at least in part on the medical surgical task prior to generating a second image frame that contains the object, the second image frame generated via exposing the subject to the radiation beam, comprises:
   adjusting at least one of an image quality of the second image frame, a frame rate between the first image frame and the second image frame, a field of view of the second image frame, and a collimation of the adjusted radiation beam.

3. The method of claim 1, wherein adjusting the radiation beam based at least in part on the medical surgical task prior to generating a second image frame that contains the object, the second image frame generated via exposing the subject to the radiation beam, comprises:
   determining a difficulty level of the medical surgical task.

4. The method of claim 3, wherein determining a difficulty level of the medical surgical task comprises:
   performing a semantic analysis of the first image frame.

5. The method of claim 4, wherein performing a semantic analysis of the first image frame comprises:
   identifying in the first image frame at least one of a number of tools, a status of a catheter, and a step of the medical surgical task.

6. The method of claim 1, wherein adjusting the radiation beam based at least in part on the medical surgical task prior to generating a second image frame that contains the object, the second image frame generated via exposing the subject to the radiation beam, comprises:
   adjusting the radiation beam such that the adjusted radiation beam conforms to a radiation exposure strategy.

7. The method of claim 6, wherein adjusting the radiation beam based at least in part on the medical surgical task prior to generating a second image frame that contains the object, the second image frame generated via exposing the subject to the radiation beam, further comprises:
   overriding the radiation exposure strategy such that the adjusted radiation beam does not conform to the radiation exposure strategy.

8. The method of claim 1, wherein identifying a medical surgical task in a first image frame that contains the object, the first image frame generated via exposing the subject to the radiation beam, comprises:
   determining in the first image frame whether the imaged object is at least one of high contrast and low contrast.

9. The method of claim 1, wherein adjusting the radiation beam based at least in part on the medical surgical task prior to generating a second image frame that contains the object, the second image frame generated via exposing the subject to the radiation beam, comprises:
   identifying a structure in the first image frame; and
   subtracting the identified structure from the first image frame.

10. The method of claim 9, wherein the subject is a patient, the imaged object is a blood vessel of the patient that is infused with a high contrast medium, and the identified structure includes at least one of an organ of the patient other than the blood vessel, and a medical device.

11. The method of claim 1, wherein the first image frame and the second image frame are based at least in part on a mask, and adjusting the radiation beam based at least in part on the medical surgical task prior to generating a second image frame that contains the object, the second image frame generated via exposing the subject to the radiation beam, comprises:
   generating an intermediate image frame via exposing the subject to the radiation beam before generating the second image frame, the intermediate image frame containing the object and based at least in part on the mask;
   comparing the first image frame with the intermediate image frame to obtain a contrast indicator; and
   adjusting the mask based at least in part on the contrast indicator.

12. A method for adjusting a radiation dose during imaging of an object within a subject, the method comprising:
   generating a first image frame that contains the object via applying a mask to a first image obtained via exposing the subject to a radiation beam;
   identifying a medical surgical task in the first image frame;
   generating a second image frame that contains the object via applying the mask to a second image obtained via exposing the subject to the radiation beam;
   comparing the first image frame with the second image frame to obtain a contrast indicator;
   adjusting the mask based at least in part on the contrast indicator; and
   adjusting the radiation beam based at least in part on at least one of the medical surgical task and the adjusted mask.

13. The method of claim 12, wherein comparing the first image frame with the second image frame to obtain a contrast indicator comprises:

detecting an area common between the first image frame and the second image frame that does not exhibit significant contrast.

14. The method of claim 12, wherein adjusting the mask based at least in part on the contrast indicator comprises: reducing the mask.

15. The method of claim 12, wherein adjusting the radiation beam based at least in part on at least one of the medical surgical task and the adjusted mask comprises:
identifying a structure in the first image frame; and
subtracting the identified structure from the first image frame.

16. An imaging system that adjusts a radiation dose during imaging of an object within a subject, the imaging system comprising:
a controller configured to generate a first image frame that contains the object via exposing the subject to a radiation beam; and
wherein the controller is further configured to identify a medical surgical task in the first image frame and adjust the radiation beam based at least in part on the identified medical surgical task prior to generating a second image frame that contains the object via exposing the subject to the radiation beam.

17. The system of claim 16, wherein the subject is a patient, the imaged object is a blood vessel of the patient that is infused with a high contrast medium, and the controller is further configured to determine a difficulty level of the identified medical surgical task.

18. The system of claim 17, wherein the controller is further configured to determine the difficulty level of the identified medical surgical task via performing a semantic analysis of the first image frame.

19. The system of claim 16, wherein the controller is further configured to adjust the radiation beam via identifying a structure in the first image frame and subtracting the identified structure from the first image frame.

20. The system of claim 16, wherein the first image frame and the second image frame are based at least in part on a mask, and the controller is further configured to generate an intermediate image frame after generating the first image frame and before generating the second image frame, the intermediate image frame containing the object via exposing the subject to the radiation beam and also based at least in part on the mask;
compare the first image frame with the intermediate image frame to obtain a contrast indicator;
adjust the mask based at least in part on the contrast indicator; and
adjust the radiation beam based at least in part on the adjusted mask prior to generating the second image frame.

21. A method for adjusting a radiation dose during imaging of an object within a subject, the method comprising:
acquiring a first series of medical images in rotation around the subject prior to injection of a contrast agent;
acquiring a second series of medical images in rotation around the subject after injection of the contract agent; and
wherein a contrast injection pattern is identified in a first image of the second series of medical images, and subsequent images of the second series of medical images acquired after the first image are optimized based at least in part on the identified contrast injection pattern.

* * * * *